US00PP18206P2

(12) United States Plant Patent
Damen

(10) Patent No.: US PP18,206 P2
(45) Date of Patent: Nov. 13, 2007

(54) ***HELENIUM* PLANT NAMED 'DOUBLE TROUBLE'**

(50) Latin Name: *Helenium hybrida*
Varietal Denomination: Double Trouble

(75) Inventor: Petrus Thomas Damen, Hillegom (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 11/450,829

(22) Filed: Jun. 9, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Helenium* plant named 'Double Trouble', characterized by its upright, somewhat outwardly spreading and uniform plant habit; moderately vigorous growth habit; freely flowering habit; inflorescences with golden yellow-colored ray and disc florets; and strong peduncles that hold the inflorescences above the foliar plane.

1 Drawing Sheet

Botanical designation: *Helenium hybrida.*
Cultivar denomination: 'Double Trouble'.

BACKGROUND OF THE INVENTION

The present invention relates to a new and distinct cultivar of *Helenium* plant, botanically known as *Helenium hybrida,* and hereinafter referred to by the name 'Double Trouble'.

The new *Helenium* is a product of a planned breeding program conducted by the Inventor in Hillegom, The Netherlands. The objective of the program is to create and develop new *Helenium* cultivars with double inflorescence form, sterile flowers and a long flowering period.

The new *Helenium* originated from a cross-pollination by the Inventor in 1998 of two unnamed selections of *Helenium hybrida,* not patented. The new *Helenium* was discovered and selected by the Inventor as a single flowering plant within the progeny of the stated cross-pollination in a controlled environment in Hillegom, The Netherlands in 1999.

Asexual reproduction of the new *Helenium* by terminal cuttings in a controlled environment in Hillegom, The Netherlands since 1999, has shown that the unique features of this new *Helenium* are stable and reproduced true to type in successive generations.

SUMMARY OF THE INVENTION

The cultivar Double Trouble has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Double Trouble'. These characteristics in combination distinguish 'Double Trouble' as a new and distinct cultivar of *Helenium:*

1. Upright, somewhat outwardly spreading and uniform plant habit.
2. Moderately vigorous growth habit.

3. Freely flowering habit.
4. Inflorescences with golden yellow-colored ray and disc florets.
5. Strong peduncles that hold the inflorescences above the foliar plane.

In side-by-side comparisons conducted in Hillegom, The Netherlands, plants of the new *Helenium* differed from plants of the parent selections primarily in inflorescence form as plants of the new *Helenium* had more ray florets than plants of the parent selections.

Plants of the new *Helenium* can be compared to plants of the *Helenium* cultivar Kanaria, not patented. In side-by-side comparisons conducted in Hillegom, The Netherlands, plants of the new *Helenium* differed from plants of the cultivar Kanaria in the following characteristics:

1. Plants of the new *Helenium* had more ray florets per inflorescence than plants of the cultivar Kanaria.
2. Plants of the new *Helenium* flowered for a longer period of time than plants of the cultivar Kanaria.
3. Plants of the new *Helenium* were sterile whereas plants of the cultivar Kanaria were not sterile.

BRIEF DESCRIPTION OF THE PHOTOGRAPH

The accompanying photograph illustrates the overall appearance of the new *Helenium.* This photograph show the colors as true as it is reasonably possible to obtain in colored reproductions of this type. Colors in the photograph may differ slightly from the color values cited in the detailed botanical description which accurately describe the colors of the new *Helenium.* The photograph comprise a close-up view of typical inflorescences of 'Double Trouble'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Hillegom, The Netherlands during the summer in an outdoor nursery and under conditions and practices which approximate those generally used in commercial *Helenium* production. During the production of the plants, day temperatures ranged from 14° C. to 31° C. and night temperatures ranged from 4° C. to 16° C. Measurements and numerical values represent averages for typical flowering plants. Plants were about one year old when the photographs and description were taken.

Botanical classification: *Helenium hybrida* cultivar Double Trouble.

Parentage:

*Female, or seed, parent.*—Unnamed selection of *Helenium hybrida,* not patented.

*Male, or pollen, parent.*—Unnamed selection of *Helenium hybrida,* not patented.

Propagation:

*Type.*—Terminal vegetative cuttings.

*Time to initiate roots.*—About two weeks.

*Time to produce a rooted cutting.*—About three to four weeks.

*Root description.*—Fine.

*Rooting habit.*—Freely branching; dense.

Plant description:

*Appearance and growth habit.*—Perennial herbaceous container and cut flower plant. Upright and somewhat outwardly spreading plant habit; inverted triangle. Freely basal branching with about six primary branches. Moderately vigorous growth habit.

*Plant height.*—About 75 cm.

*Plant width or area of spread.*—About 46 cm.

*Lateral branch description.*—Appearance: Mostly rounded with four vertical "wings"; wings about 2 mm in depth and dull in appearance. Length: About 59 cm. Diameter: About 6 mm. Internode length: About 2.7 cm. Strength: Strong. Texture: Smooth, glabrous. Color: 144B; wings, 143A.

Foliage description:

*Arrangement.*—Alternate; simple; sessile.

*Length.*—About 12.7 cm.

*Width.*—About 2.1 cm.

*Shape.*—Narrowly elliptic to oblanceolate.

*Apex.*—Acute.

*Base.*—Cuneate; decurrent.

*Margin.*—Dentate.

*Venation pattern.*—Pinnate.

*Texture, upper and lower surfaces.*—Smooth, glabrous.

*Color.*—Developing foliage, upper surface: 143A. Developing foliage, lower surface: 143B. Fully expanded foliage, upper surface: 137A; venation, 144A. Fully expanded foliage, lower surface: 137C; venation, 144A.

Inflorescence description:

*Appearance/arrangement.*—Single terminal and axillary inflorescences held above the foliage on strong erect peduncles. Composite inflorescence form, radially symmetrical; flabellate-shaped ray florets; disc florets massed at the center; ray and disc florets develop acropetally on a capitulum. Inflorescences face mostly upright.

*Flowering response.*—Plants flower continuous and freely from midsummer to late summer in The Netherlands. Inflorescences persistent.

*Postproduction longevity.*—Inflorescences maintain good color and substance for about three weeks on the plant and about two weeks as cut flowers.

*Quantity of inflorescences.*—Freely flowering habit; about 144 inflorescences per plant develop during the flowering season.

*Fragrance.*—None detected.

*Inflorescence bud.*—Length: About 7 mm. Diameter: About 1.1 cm. Shape: Flattened globular. Color: N144A.

*Inflorescence size.*—Diameter: About 4.6 cm. Depth (height): About 2.1 cm. Disc diameter: About 1.6 cm. Receptacle height: About 5 mm. Receptacle diameter: About 6 mm.

*Ray florets.*—Length: About 2 cm. Width: About 1.2 cm. Shape; Flabellate. Apex: Incised to lacinate. Base: Attenuate. Margin: Entire. Texture, upper and lower surfaces: Mostly smooth; towards the base, pubescent. Orientation: Initially upright then perpendicular to the peduncle. Number of ray florets per inflorescence: About 16 in a single whorl. Color: When opening, upper surface: 13A. When opening, lower surface: 14B. Fully opened, upper surface: 14B. Fully opened, lower surface: 13B.

*Disc florets.*—Shape: Tubular, elongated. Apex: Five-pointed: acute. Length: About 3 mm. Width, apex: About 1 mm. Width, base: About 0.8 mm. Number of disc florets per inflorescence: Numerous, about 600. Color, immature: 150B; towards the apex, 153A to 153B. Color, mature: Apex: 153C. Mid-section: 151B. Base: 145D.

*Phyllaries.*—Length: About 1.2 mm. Diameter: About 1.5 mm. Shape: Linear. Apex: Acute. Base: Cuneate. Margin: Entire. Texture, upper and lower surfaces: Smooth, glabrous. Number per inflorescence: About 16 in a single whorl. Color, upper surface: 143B. Color, lower surface: 143A.

*Peduncles.*—Length, terminal peduncle: About 10.5 cm. Length, fourth peduncle: About 26.4 cm. Length, seventh peduncle: About 27.4 cm. Diameter: About 2 mm. Angle: Mostly erect to about 10° from vertical. Strength: Moderately strong. Texture: Smooth, glabrous. Color: 143A to 143B.

*Reproductive organs.*—None observed; inflorescences sterile.

*Fruit/seed.*—Fruit and seed development have not been observed.

Disease/pest resistance: Resistance to pathogens and pests common to *Helenium* has not been observed on plants grown under outdoor conditions.

Garden performance: Plants of the new *Helenium* have been observed to have good garden performance and to tolerate rain, wind and temperatures from about 0° to about 35° C.

It is claimed:

1. A new and distinct *Helenium* plant named 'Double Trouble' as illustrated and described.

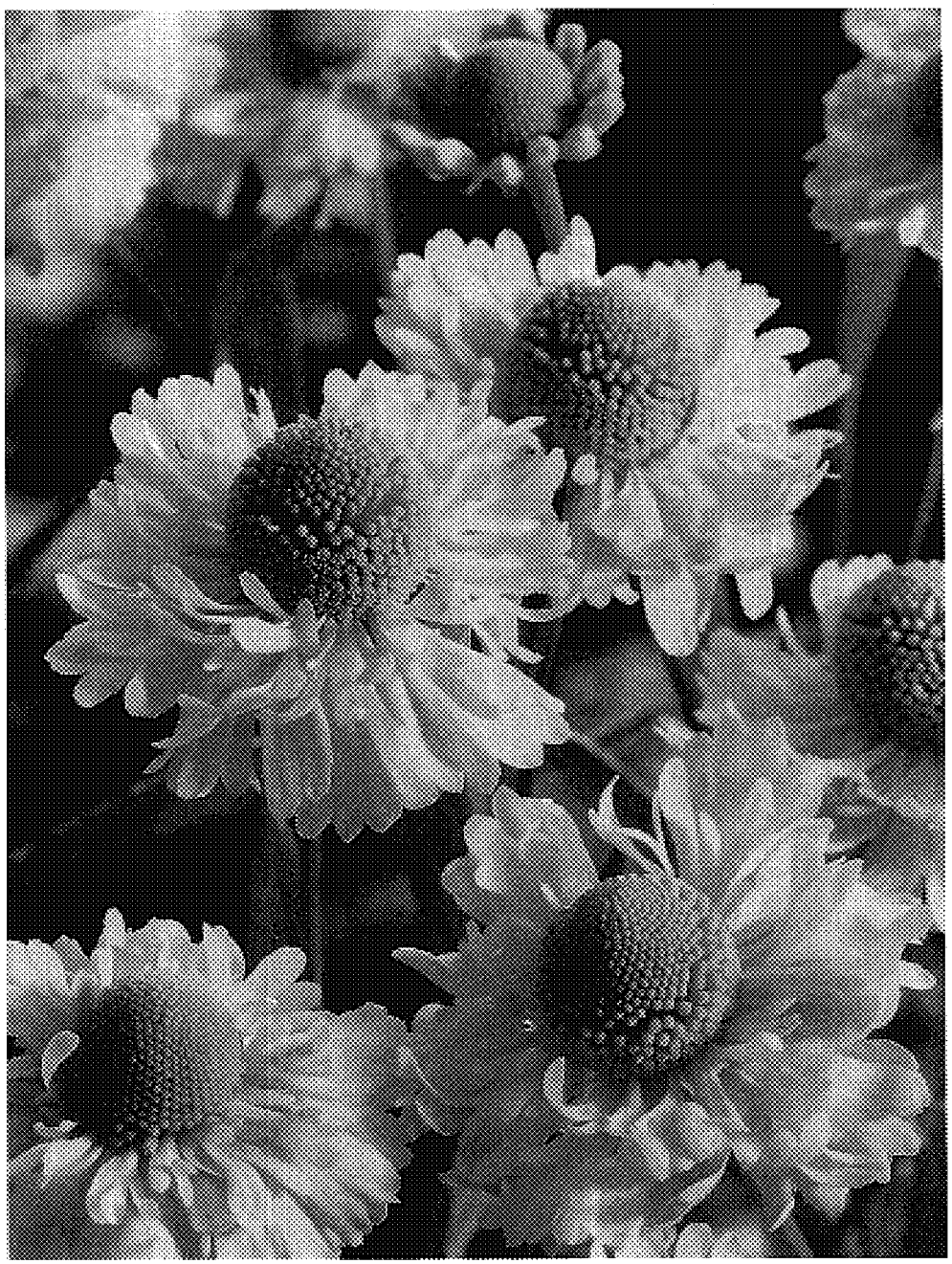

* * * * *